US006888486B2

(12) United States Patent
König

(10) Patent No.: US 6,888,486 B2
(45) Date of Patent: May 3, 2005

(54) APPARATUS FOR PRODUCING A NATURAL ELECTROMAGNETIC ALTERNATING FIELD CLOSE TO THE BODY

(76) Inventor: Florian Meinhard König, Schellenborgstrasse 7, D-82110 Germering (DE)

( * ) Notice: Subject to any disclaimer, the term of this patent is extended or adjusted under 35 U.S.C. 154(b) by 0 days.

(21) Appl. No.: 10/414,981

(22) Filed: Apr. 16, 2003

(65) Prior Publication Data

US 2003/0231126 A1 Dec. 18, 2003

(30) Foreign Application Priority Data

Apr. 17, 2002 (DE) .......................................... 102 17 083

(51) Int. Cl.[7] .............................. H03M 1/66; A61N 1/08
(52) U.S. Cl. ......................... 341/144; 341/148; 600/13; 607/50
(58) Field of Search ........................ 600/9–15; 307/91, 307/104; 341/155, 144, 148

(56) References Cited

U.S. PATENT DOCUMENTS 5,566,685 A * 10/1996 Litovitz et al. ............. 128/898
6,312,376 B1 * 11/2001 Koren et al. .................. 600/13
6,369,399 B1 * 4/2002 Smirnov .................. 250/515.1
6,527,696 B1 * 3/2003 Kim ............................. 600/13
6,547,713 B1 * 4/2003 Talpo ............................ 600/9
6,675,047 B1 * 1/2004 Konoplev et al. ............ 607/50

OTHER PUBLICATIONS

Internet Advertisement for the "MicroHarmonizer" Energy Tools, Inc. copyright 2002 http://www.energytools.biz/micro_harmonizer.html Page Accessed Jan. 8, 2004.*
"*Magazine 2000 plus*, No. 144 (Dec. 1999, p. 74), Liebrecht von Klitzing".
Herbert L. König "*unsichtbare Umwelt*" [*invisible environment*], Munich, 1986).
"*MEDISENT*", www.magnet–feldtherapie–2000.de.

* cited by examiner

*Primary Examiner*—Howard L. Williams
(74) *Attorney, Agent, or Firm*—Collard & Roe, P.C.

(57) ABSTRACT

An apparatus for producing a natural electromagnetic alternating field close to a user's body. The natural electromagnetic alternating field is similar to an area of pleasant weather (Sferics), to compensate for electrical stress acting on a user. The field can also be used for positive stimulation of the well-being of the user. The apparatus has a means for producing the alternating field and a means for transmitting the alternating field.

18 Claims, 5 Drawing Sheets

APPARATUS FOR PRODUCING A NATURAL ELECTROMAGNETIC ALTERNATING FIELD CLOSE TO THE BODY

BACKGROUND

The invention relates to an apparatus for producing a natural electromagnetic alternating field close to a person's body.

Our environment is affected by numerous electromagnetic alternating fields. A large proportion of these electromagnetic alternating fields are artificial, and thus are produced by man. One prominent example of such fields are artificially produced electromagnetic fields for data transmission up to the gigahertz range. Mobile telephones, such as cell phones, operate using the GSM data transmission format and, in the future, will use the UMT data transmission format as well. These electromagnetic fields are typically pulsed around 100 Hz or around 217 Hz. These fields can cause severe electrical stress, which has a disadvantageous effect on organic cells. The high transmission power from mobile phones when the respective handset is used close to the ear of the user causes unavoidable considerable biological stress acting on the organic cells of the user. In scientific publications and, inter alia, in the magazine 2000 plus, No. 144 (12-1999, page 74), Liebrecht von Klitzing has stated that the wide dynamic range of more than 60 dB between the pulse packages of the RF signal transmission is a source of severe cell stimulus/irritation, with a typical cell resonance of up to 400 Hz. Furthermore, this article states that the signal periodicity represents a significant factor in the influence on cells, and that a stochastic signal response will be considerably better for the organic cells, since it is less damaging. Furthermore, sufficient knowledge is available about the disadvantageous biological effects of artificial radio-frequency fields on the organic cells of living beings, or people (see, for example, Herbert L. König "unsichtbare Umwelt" [invisible environment], Munich, 1986).

However, the human body is also affected by natural electromagnetic alternating fields. For example, it is known that certain weather situations, for example föhn weather in the alpine area, are associated with natural electromagnetic alternating fields which propagate horizontally and/or vertically and are in the range between a few 100 Hz and, typically, 50 000 Hz. Such "areas of bad weather" have a disadvantageous effect on living beings in a manner that is known. In contrast to this, areas of pleasant weather, which are also referred to as Sferics, are known, which have a positive effect on living beings. These natural electromagnetic alternating fields are also in the range from a few 100 Hz up to, typically, at least 20 kHz and, in contrast to areas of bad weather, have a different amplitude and frequency distribution.

It is also known for a battery-powered pocket device to be used for stimulation of human beings and to compensate for certain disadvantageous influences on the human organism. The device interferes with and compensates for electrical smog, which produces artificial electromagnetic alternating fields in the very low frequency range between 1.4 and 32.4 Hz. See, "MEDISENT", www.magnet-feldtherapie-2000.de). Higher frequency electromagnetic alternating fields, such as electrical smog in the AF band above 30 Hz and in the RF band, are not considered by this device.

SUMMARY OF THE INVENTION

One object of the present invention to provide an apparatus which makes it possible to compensate for electrical stress acting on a user, at least essentially independently of amplitude and frequency, and/or makes it possible to positively stimulate the well-being of a user.

Accordingly, the present invention provides an apparatus for producing a natural electromagnetic alternating field close to the body, such as an area of beneficial electromagnetic waves to compensate for electrical stress acting on a user and for positive stimulation of the well-being of the user. This apparatus has a means for producing the alternating field, and has a means for transmitting the alternating field.

The invention is based on the knowledge that both natural and artificial electromagnetic alternating fields which have a disadvantageous influence on living beings or users can be compensated for by producing an opposing field, such as a natural electromagnetic alternating field. This field provides known positive effects. Alternatively, such an opposing field may also contribute to positive stimulation of the well-being of a user. Areas of beneficial electromagnetic waves have been found to be particularly suitable for use as the opposing field.

According to the invention, the opposing field in the form of a natural electromagnetic alternating field is produced close to the body. Close to the body here means that the source of an electromagnetic alternating field is located immediately against the body, for example in the area of a piece of clothing worn by a user, and in the immediate vicinity of the user's location. This may be the living area, a motor vehicle passenger compartment, or a building. This area is generally bounded by a far area, which is defined by the area which is adjacent to the area immediately surrounding a user. This area may be outside the room or the building in which a user is located.

The apparatus according to the invention can comprise an alternating field production means and an alternating field transmission means. These two means are advantageously accommodated in a common housing, which is positioned in the near field of a user and may be worn immediately against the body of a user on a piece of clothing. In the last-mentioned case, the housing may be in the form of a biro or, alternatively, in the form of a flat container. If this unit is used in the near area of a user, but is not worn on the body, it may be integrated in a piece of furniture, particularly in a chair, or else in the area of the passenger compartment of a motor vehicle or some other vehicle, including an aircraft or a water craft.

The apparatus according to the invention may also be contained in a device which produces artificial electromagnetic fields which are to be compensated for by the apparatus according to the invention. These devices can be in a mobile telephone or a cordless telephone, a headset, in components of an audio/video system, or any similar type system.

In one embodiment of the invention, the means for transmitting the natural electromagnetic alternating field includes "transmitting antennas" which are already present in the vicinity of the user. These "transmitting antennas" may include the protective contact ground of a building, connecting cables for a telecommunications connection, or else a Faraday cage, such as the bodywork of a vehicle, such as a motor vehicle, an aircraft or a ship, or other transmission means within these environments.

The means for producing the natural electromagnetic alternating field advantageously comprises a memory in which this alternating field is stored, preferably in digital form. Alternatively, two or more alternating fields are stored in digital form in the memory and can be called up from this memory for application to the transmission means, preferably as a function of the time of day. The data for producing an electromagnetic field relating to an area of pleasant weather (Sferics) are preferably stored in the memory, with the data for this area of pleasant weather being recorded in situ, then converted in digital form and stored in the memory.

Depending on the requirement, it is also possible to mix the natural electromagnetic alternating field with artificial electromagnetic alternating fields which may likewise be stored in digital form in a memory. The natural electromagnetic field then compensates for the electrical stress caused by the artificial electromagnetic field and/or contributes to positive stimulation of the well-being of a user. One artificial electromagnetic alternating field which may be quoted here, is, for example, a very low frequency signal, such as a broadband pulse in the frequency range from 0.01 to 40 Hz, preferably 0.1 to 32 Hz (very low frequency band).

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION

Figure 1:
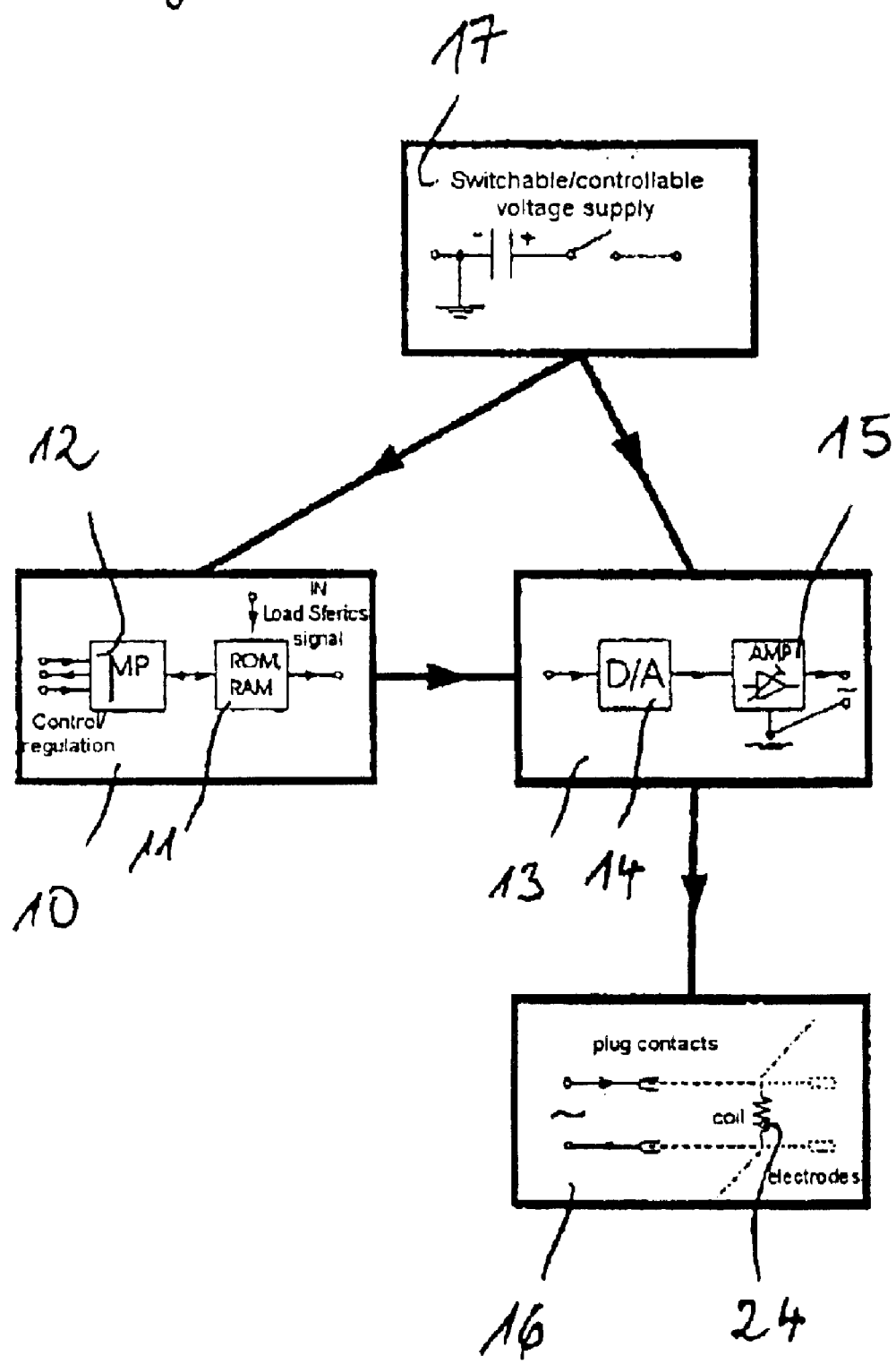
FIG. 1 shows a block diagram of an apparatus according to the invention.

Referring to the drawings, FIG. 1 shows the apparatus according to the invention for producing a natural electromagnetic alternating field close to the body. The apparatus has a memory device 10 in which the electromagnetic alternating field, or two or more such alternating fields, is or are stored in digital form. Memory device 10 contains a ROM or RAM 11 and a control circuit or selection device 12, which allows the data for a respective electromagnetic alternating field to be called up from ROM or RAM 11 and can be specifically provided at the output of ROM or RAM 11. For example, control circuit 12 can receive a set of instructions from a plurality of different data sets stored in ROM or RAM 11 to produce a field of electromagnetic waves similar to Sferics. In addition, control circuit 12 can receive a set of instructions from ROM or RAM 11 to provide natural electromagnetic alternating fields in a cyclical on/off manner to produce fading. In another example, control circuit could receive instructions from ROM or RAM 11 to provide differing electromagnetic fields corresponding to the time of day.

The output of memory device 10 is connected to a digital to analog D/A converter unit 13, in which the digital data produced at the output of memory device 10 is converted to analog signals. For this purpose, device 13 has a D/A converter module 14, which receives on the input side the output signal from device 10. Device 10 also contains a variable gain amplifier 15, which is connected to the output of D/A converter module 14 and which produces the analog signals at a specific amplitude on the output.

Converter unit 13 is coupled to or is in communication with transmission device 16 so that the output signal from amplifier 15 or from converter unit 13 is sent to transmission device 16, which transmits the natural electromagnetic alternating field so that it can be absorbed by a user, close to the body. Transmission device 16 can be connected to a transmission antenna, for example the protective ground contact of a building, or to the bodywork of a vehicle, to transmit the natural electromagnetic alternating field to a user within a building or the vehicle, or to some other occupant in the passenger compartment of a vehicle. For example, FIGS. 3 and 4 show a capsule of a headset, which is designed to transmit the natural electromagnetic alternating field in an inaudible manner as described in detail in the following text.

The apparatus according to the invention illustrated in FIG. 1 also has a power supply unit 17 for supplying power to the devices 10, 13 and 16.

Figure 2:
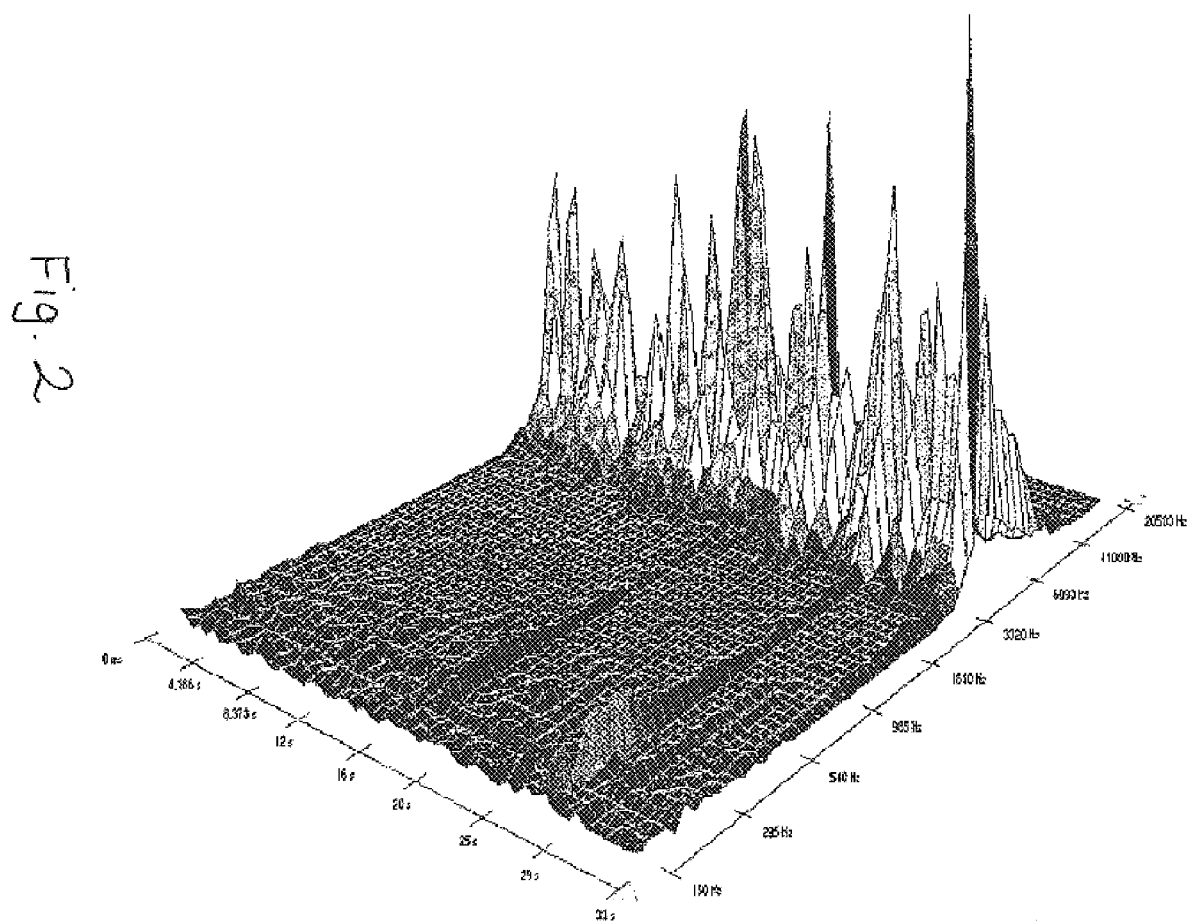
FIG. 2 shows an extract of a typical area of beneficial electromagnetic fields over a restricted frequency band, which is stored in digital form in the apparatus shown in FIG. 1.

FIG. 2 shows a narrowband extract or restricted-frequency example of a natural electromagnetic alternating field in the form of an area of pleasant electromagnetic waves (Sferics), which is sampled after being recorded and is stored as one of the alternating fields in memory device 10.

Figure 3:
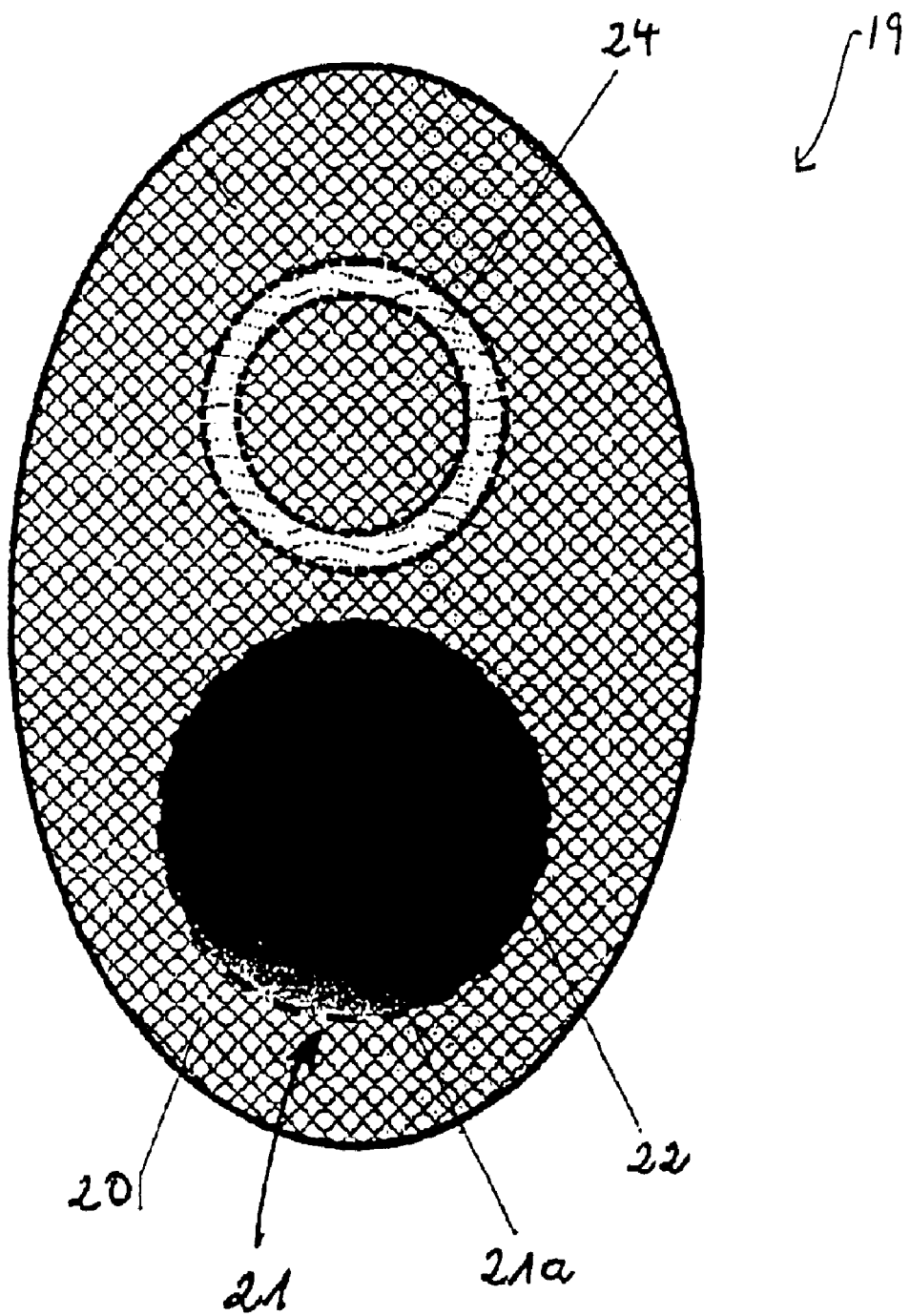
FIG. 3 shows a front side view of the apparatus in FIG. 1 stored in a sound wall in the capsule of a headset.
Figure 4:
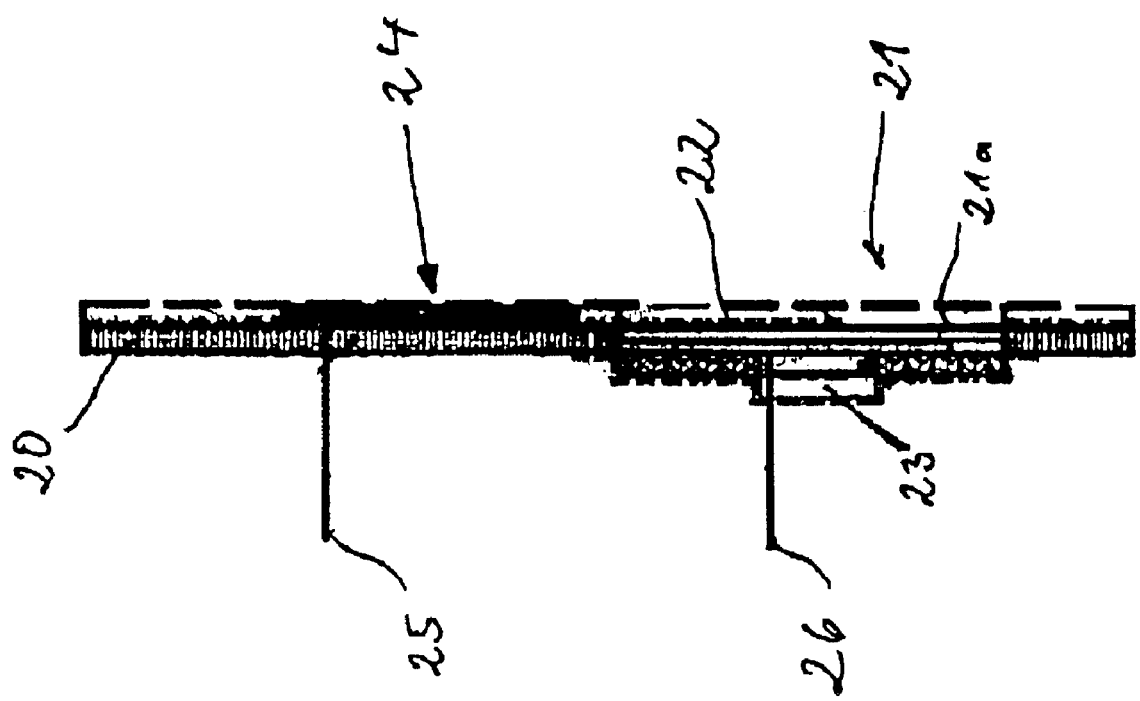
FIG. 4 shows a longitudinal section view of the sound wall from FIG. 3, along its longitudinal center axis.

FIGS. 3 and 4 show a sound wall 20 of a headset capsule 19 which is generally elliptical in shape and has a circular aperture in its lower area. This aperture has a sound transducer 21 and also there is a sound panel 22 which is arranged to convey a sound which is perceived as being centrally in front of a user. Sound panel 22 partially covers membrane 21a of sound transducer 21.

FIG. 4 shows membrane 21a of sound transducer 22 which is driven in a conventional manner by an electromagnet drive. The electromagnetic drive is seated on the rear face of the membrane and is connected to it. This drive has a coil 23 through which a useful signal current flows and which produces an artificial electromagnetic alternating field. This artificial electromagnetic alternating field is in contrast to the opposing field according to the invention, which is a natural electromagnetic alternating field. The artificial electromagnetic field causes electrical stress to a user because of its proximity to the temple of a user. To compensate for this electrical stress, a toroidal coil 24 is disposed at a distance from sound transducer 21, through which the longitudinal center axis of sound wall 20 passes. Coil 24, which is also shown schematically as a component of device 16 in FIG. 1 produces a natural electromagnetic alternating field at the output of amplifier 15, via connections 25 and 26. In addition, as an alternative to coil 24, some other antennas for transmission of an opposing field may be considered for the electromagnetic field of sound transducer 21. This natural electromagnetic alternating field which is produced by coil 24, compensates for the disadvantageous effects of sound wall 20 which lead to electrical stress, from the artificial electromagnetic alternating field. This field is produced by coil 23 of the sound transducer drive. The apparatus 10, 13, 16 according to the invention is preferably integrated in the headset capsule or capsules.

Figure 5A:
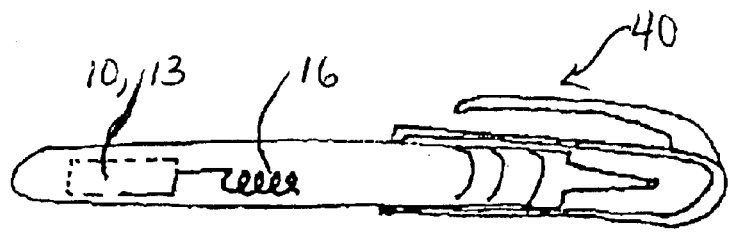
FIG. 5A shows a side view of the device in a second type housing.

FIG. 5A shows the device wherein the means for producing the natural electromagnetic field in the form of a memory device 10 and the converter unit 13 and the means for transmitting the natural electromagnetic field in the form of a transmission device 16 are all housed inside of a pen housing 40.

Figure 5B:
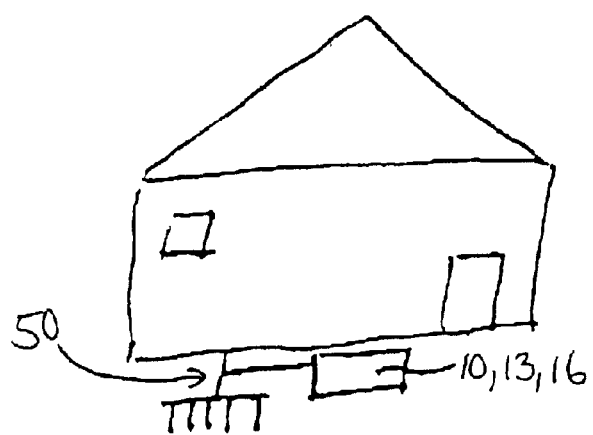
FIG. 5B shows a schematic view of the device being connected to a ground on a housing.

FIG. 5B shows the device according to the invention being coupled to a contact ground 50 of a building.

Accordingly, while at least one embodiment of the present invention has been shown and described, it is to be understood that many changes and modifications may be made thereunto without departing from the spirit and scope of the invention as defined in the appended claims.

What is claimed is:

1. An apparatus for producing a natural electromagnetic alternating field close to a user's body to compensate for external electromagnetic fields acting on a user, the apparatus comprising:
    a) a means for producing the natural electromagnetic alternating field wherein said means includes a memory device which stores predetermined sets of frequencies for electromagnetic fields; and
    b) a means for transmitting the natural electromagnetic alternating field.

2. The apparatus as in claim 1, further comprising a housing wherein said means for producing the natural electromagnetic alternating field is disposed in said housing and said means for transmitting the natural electromagnetic alternating field is disposed in said housing.

3. The apparatus as in claim 2, wherein said housing is adapted to be worn on a piece of clothing on a user.

4. The apparatus as in claim 2, wherein said housing is a chair.

5. The apparatus as in claim 2, wherein said housing is a vehicle seat.

6. The apparatus as in claim 5, wherein said vehicle is an airplane.

7. The apparatus as in claim 2, wherein said housing is a headset for listening to music.

8. The apparatus as in claim 2, wherein said housing is chosen from a group consisting of headsets, components of an audio/video system, mobile telephones, cordless telephones and a computer.

9. The apparatus as in claim 1, wherein said memory element stores a plurality different data sets defining different alternating magnetic fields and said apparatus further comprises a selection device for selecting at least one of said natural electromagnetic alternating fields.

10. The apparatus as in claim 9, further comprising a means for producing an artificial electromagnetic alternating field which is in a low frequency range between 0.1 and 40 Hz or in an ECF band wherein said artificial alternating field is mixed with said natural alternating field and wherein both of said fields are fed into said transmission means.

11. The apparatus as in claim 9, wherein at least one of said plurality of different data sets defines a natural electromagnetic alternating field that is in a form of at least one field of electromagnetic waves similar to Sferics.

12. The apparatus as in claim 9, wherein said memory element is programmed with a set of instructions to control said selection device so that said production means and said transmission means provide natural electromagnetic alternating fields in a cyclical manner in an alternating on/off manner to produce fading.

13. The apparatus as in claim 4, wherein said memory element is programmed with a set of instructions to control said selection device so that said means for producing said natural electromagnetic alternating field and said means for transmitting said natural electromagnetic alternating field provide differing electromagnetic fields corresponding to the time of day.

14. The apparatus as in claim 1, wherein said means for transmitting said natural electromagnetic alternating field is coupled to a contact ground of a building.

15. The apparatus as in claim 1, wherein said means for transmitting said natural electromagnetic alternating field is coupled to at least one connecting cable of a telecommunications connector.

16. The apparatus as in claim 1, wherein said means for transmitting said natural electromagnetic alternating field is coupled to a bodywork of a vehicle to provide an electromagnetic influence on a user.

17. An apparatus for producing a natural electromagnetic alternating field close to a user's body to compensate for external electromagnetic fields acting on a user, the apparatus being disposed in a headset and coupled to a power supply, the apparatus comprising:
    a) a memory device which stores predetermined sets of frequencies for electromagnetic fields, said memory device having a output, wherein said memory device is disposed in said headset and coupled to the power supply, said memory device comprising:
        i) a read only memory; and
        ii) a control circuit in communication with said read only memory;
    b) a digital to analog converter unit having an output, and being coupled to said power supply and in communication with said memory device, said digital to analog converter unit comprising:
        i) a digital to analog converter module for receiving digital data produced at an output of said memory device; and
        ii) a variable gain amplifier, which is connected to an output of said digital to analog converter module; and
    c) a transmission device comprising a coil for receiving a signal from said digital to analog converter unit and for transmitting the natural electromagnetic field to a user.

18. An apparatus for producing a natural electromagnetic alternating field close to a user's body to compensate for external electromagnetic fields acting on a user, the apparatus being disposed in a headset and coupled to a power supply, the apparatus comprising:
    a) a memory device having a predetermined set of frequencies relating to electromagnetic fields, said memory device having a output, wherein said memory device is disposed in said headset and coupled to the power supply, said memory device comprising:
        i) a random access memory unit; and
        ii) a control circuit in communication with said random access memory unit;
    b) a digital to analog converter unit having an output, and being coupled to said power supply and in communication with said memory device, said digital to analog converter unit comprising:
        i) a digital to analog, converter module for receiving digital data produced at an output of said memory device; and
        ii) a variable gain amplifier, which is connected to an output of said digital to analog converter module; and
    c) a transmission device comprising a coil for receiving a signal from said digital to analog converter unit and for transmitting the natural electromagnetic field to a user.

* * * * *